Figure 1:
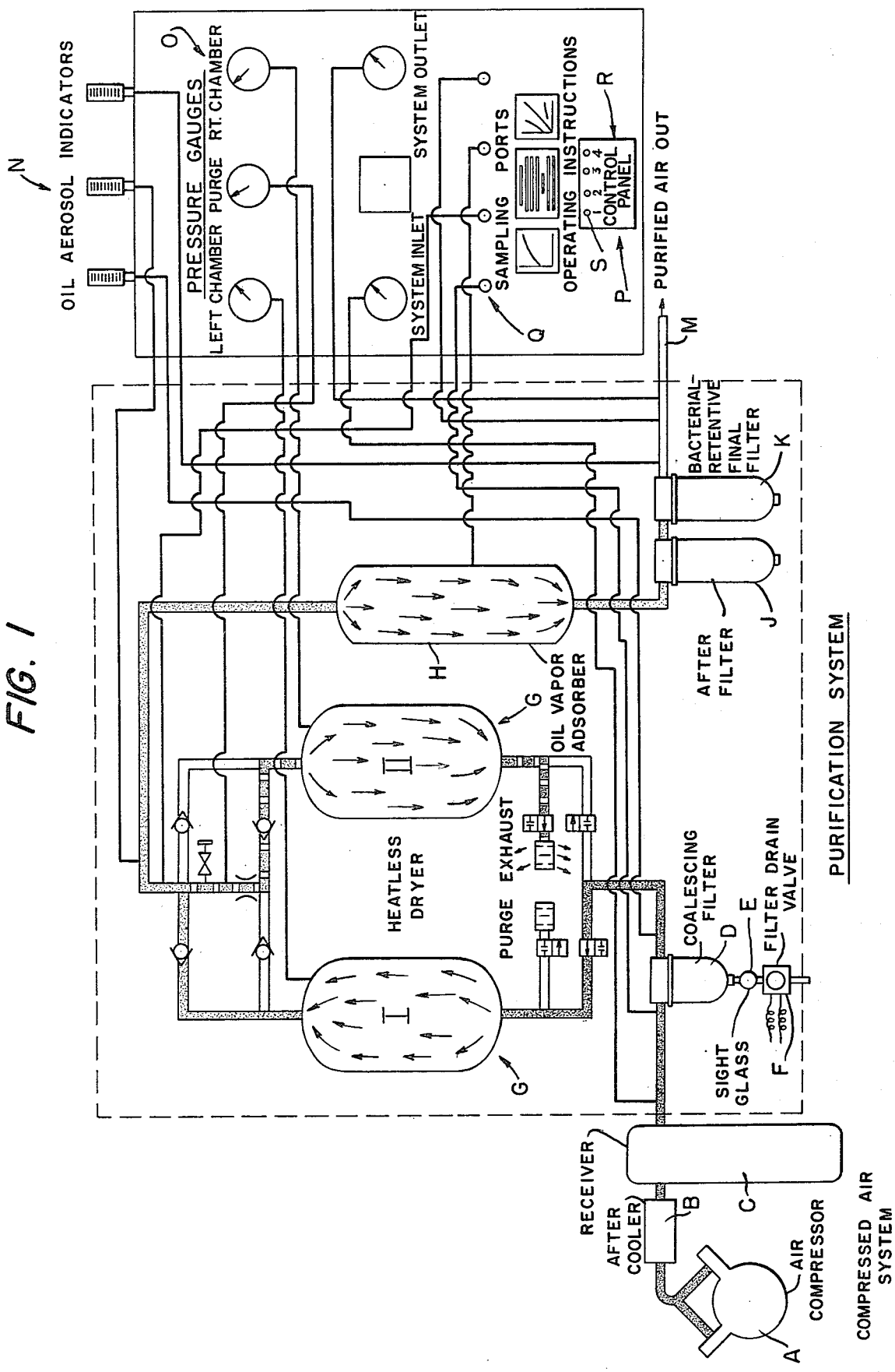

United States Patent [19]

Seibert et al.

[11] 4,231,768
[45] Nov. 4, 1980

[54] AIR PURIFICATION SYSTEM AND PROCESS

[75] Inventors: Chesterfield F. Seibert, Cortland; John D. Miller, Homer, both of N.Y.

[73] Assignee: Pall Corporation, Glen Cove, N.Y.

[21] Appl. No.: 947,310

[22] Filed: Sep. 29, 1978

[51] Int. Cl.³ .................... B01D 53/04; B01D 53/26
[52] U.S. Cl. .................... 55/179; 55/275; 55/316; 55/387; 55/389; 55/487; 210/DIG. 5
[58] Field of Search .................... 55/33, 58, 62, 68, 74, 55/75, 161, 162, 179, 275, 316, 387, 389, 487; 210/DIG. 5

[56] References Cited

U.S. PATENT DOCUMENTS

| | | | |
|---|---|---|---|
| 2,096,851 | 10/1937 | Fricke | 55/316 X |
| 2,771,153 | 11/1956 | Hennig | 55/487 X |
| 2,883,345 | 4/1959 | Taylor et al. | 210/DIG. 5 |
| 2,888,095 | 5/1959 | Perrini et al. | 55/487 |
| 3,448,561 | 6/1969 | Seibert et al. | 55/33 X |
| 3,490,205 | 1/1970 | Hauser | 55/179 |
| 3,796,025 | 3/1974 | Kasten | 55/316 |
| 3,930,813 | 1/1976 | Gessner | 55/68 X |
| 3,951,814 | 4/1976 | Krueger | 210/DIG. 5 |

FOREIGN PATENT DOCUMENTS 862074  3/1961  United Kingdom .............. 55/162

OTHER PUBLICATIONS

HX Automatic Dryer, Bulletin HX-320, Pall Trinity Micro Corp., 1963, 4 pages.

*Primary Examiner*—Robert H. Spitzer

[57] ABSTRACT

An air purification system and process are provided that are capable of ensuring oil-free moisture-free and particulate- and microbial contaminant-free pharmaceutical quality air, the air purification system comprising, in combination, and in the sequence indicated:
(1) an oil and water coalescer filter;
(2) an adsorbent or desiccant dryer;
(3) an oil vapor adsorber;
(4) an after-filter; and
(5) a bacterial-retentive final filter.

38 Claims, 6 Drawing Figures

AIR PURIFICATION SYSTEM AND PROCESS

SUMMARY OF THE PRIOR ART

The proposed *Current Good Manufacturing Practices for Large Volume Parenterals* and *The Request for Comments Regarding Small Volume Parenterals* set out the specifications for pharmaceutical-quality compressed air. These standards are very rigorous, and extremely difficult to meet.

The standards are set forth in Paragraphs 212.221 to 212.223, inclusive, as published in the *Federal Register* of Tuesday, June 1, 1976:

"§ 212.221 *Air in controlled environment areas*

"Air in controlled environment areas shall have:

"(a) A per-cubic-foot particle count of not more than 100,000 in a size range of 0.5 micron and larger when measured with automatic counters, or 700 particles in a size range of 5.0 microns or larger when measured by a manual microscopic method.

"(b) A temperature of 72° F. ±5° or 22° C. ±3°.

"(c) A maximum relative humidity of 50 percent and a minimum of 30 percent.

"(d) A positive pressure differential of at least 0.05 inch of water with all doors closed in relation to less clean adjacent areas.

"(e) At least 20 air changes per hour."

"§ 212.222 Air over filling lines and at microbiological testing sites

"Air over filling lines and at microbiological testing sites shall:

"(a) Have a per-cubic-foot particle count of not more than 100 in a size range of 0.5 micron and larger throughout the entire work area upstream of the work piece.

"(b) Be supplied at the point of use as specified in § 212.77."

"§ 212.223 Compressed Air

"Compressed air used in manufacturing and processing operations, including the sterilization process, shall be:

"(a) Filtered at points of use to meet the requirements of the area:

"(1) Compressed air to be used in the sterilizer after the sterilization process shall meet the requirements of § 212.222(a) for particle count and size.

"(2) Compressed air to be used at the filling line or microbiological testing area shall meet the requirements of § 212.222(a) for particle count and size.

"(3) Compressed air to be used in controlled environment areas shall meet the requirements of § 212.221(a) for particle count and size.

"(b) Supplied by an oil-free compressor and be free of oil and oil vapor unless vented directly to a noncontrolled environment area.

"(c) Dehumidified to prevent condensation of water vapor in the pipes."

Accordingly, pharmaceutically-acceptable air must be substantially free of oil and water droplets and vapor as well as particulate and microbial contamination, if it is to be used in manufacturing or processing operations concerning pharmaceuticals, and is not vented to a non-controlled-environment area.

It might be supposed that elimination of oil-lubricated compressors in supplying pharmaceutical-quality compressed air will ensure that the air is completely free of such contaminants. However, this is not correct. The presence of wide ranges of hydrocarbons including oil droplets and oil vapors in the ambient air in a manufacturing plant is rather common. Indeed, there are considerable amounts of hydrocarbons and especially oil droplets and oil vapor in atmospheric air in the environment of large cities. These can be present as stable aerosols and mists, smog, fog or smoke. Such air bearing hydrocarbon droplets and vapors if providing the input to the suction side of a non-oil lubricated compressor will emerge as compressed air with an undesirably increased concentration of oil and oil vapor, due to the compression.

For example, the *Journal of the Air Pollution Control Association,* April, 1976, lists the amounts of atmospheric hydrocarbons in Central Los Angeles as determined by gas chromatographic analysis in 1973, as follows:

| Hydrocarbon | Carbon ppm | Percent |
|---|---|---|
| Methane | 3.01 | 37.8 |
| Ethane | 0.125 | 1.6 |
| n-Butane | 0.149 | 1.9 |
| Isopentane | 0.193 | 2.4 |
| $C_3$ + paraffin | 2.87 | 36.0 |
| Ethane | 0.204 | 2.6 |
| Propene | 0.049 | 0.6 |
| $C_4$ + olefin | 0.084 | 1.1 |
| Acetylene | 0.178 | 2.2 |
| Benzene | 0.126 | 1.6 |
| Toluene | 0.156 | 2.0 |
| Unknown + aromatic[1] | 1.04 | 13.0 |
| Total | 7.97 | 100 |
| Non-methane | 4.96 | 62.2 |

[1]$C_8$ + aromatics and other higher molecular weight compounds not specifically identified.

Such air will emerge from the high-pressure side of the compressor with a higher concentration of hydrocarbon vapor than the ambient air, even though no oil vapor has been contributed by the compressor itself.

The use of oil-free compressors is therefore not the answer to meeting the high requirements of the proposed standards. Such compressors may lessen the addition of further hydrocarbons to the air, but will concentrate and not remove any existing hydrocarbon content of the air.

The compressor and distribution system can also serve to contribute particulate solids contamination, and particularly microbial contamination, since bacteria can grow within a nonsterile air distribution system, and their growth can be encouraged by condensation of moisture there, due to insufficiently dehumidified air. Accordingly, in order to meet the proposed standard for compressed air, it is absolutely essential to remove from ambient air not only hydrocarbon droplets and hydrocarbon vapors, but also all moisture and particulate microbial contamination.

SUMMARY OF THE INVENTION

In accordance with the invention, an air purification system is provided that is capable of doing exactly that, and it does so from compressed air, thereby ensuring oil-free moisture-free and particulate- and microbial contaminant-free pharmaceutical-quality compressed air, ready for immediate application under the proposed standard.

The air purification system in accordance with the invention comprises, in combination, and in the sequence indicated:

(1) a coalescer filter separating and removing hydrocarbon droplets and water droplets;

(2) an adsorbent dryer sorbing water vapor and hydrocarbon aerosols at least in part on particulate desiccant;

(3) an oil vapor adsorber sorbing hydrocarbon vapor and hydrocarbon aerosols at least in part on particulate activated sorbent;

(4) an after-filter separating and removing particulate solids larger than bacterial dimensions; and (5) a bacterial-retentive final filter separating and removing particulate solids of bacterial dimensions and any remaining hydrocarbon aerosol.

Because of the extremely small pores required for high efficiency aerosol separation, the coalescer filter provides quantitative particulates removal. This greatly extends the life of downstream components, especially the dryer desiccant.

SUMMARY OF THE DRAWINGS

FIG. 1 represents a flow diagram showing each of the components and its function of the air purification system of the invention, in combination with an air compressor, and a receiver;

FIG. 2 represents a flow diagram showing the cycling and structural details of the heatless desiccant dryer of FIG. 1;

FIG. 3 represents a detailed view in longitudinal section of the oil and water coalescer filter shown in FIG. 1;

FIG. 4 represents a detailed view in longitudinal section of the oil vapor adsorber shown in FIG. 1;

FIG. 5 represents a detailed view in longitudinal section of the after-filter of all-cellulose or all-polypropylene fiber resin-binder-free filter medium shown in FIG. 1; and FIG. 6 represents a detailed view in longitudinal section of the bacterial-retentive final filter shown in FIG. 1.

GENERAL DESCRIPTION OF FIG. 1

The air purification system shown in FIG. 1 has a typical plant compressed air system and includes an air compressor, an aftercooler (to bring the hot compressed air down to an acceptable temperature) and a receiver (to maintain reasonable system pressures during periods of fluctuating flow rate), all of conventional type. The system is designed to optimize a system fed by any oil lubricated compressor, but works equally well with a non-lubricated compressor.

During the compression stroke of an oil-lubricated compressor, air temperatures reach 400° F. Some of the lubricating oil in the chamber is vaporized, some is broken down to lower molecular weight hydrocarbons, while some is oxidized to produce oxidized hydrocarbons. Such hot air has to be cooled before use, in mose cases, and, upon cooling, these vapors condense and form droplets or mists having liquid droplets in the 0.01 to 50 μm size. 99% of these droplets range in size from 0.1 to 0.5 μm and these droplets are entrained in the air delivered by the compressor.

Such extremely small droplets cannot be removed by centrifugal separators because they are too small in size, and therefore in mass. Droplets below 5 μm normally pass straight through such separators.

The oil and water coalescer filter will remove upwards of 99.99% of such droplets of hydrocarbons and water in the air downstream of the air compressor/after-cooler/receiver. Quantitative removal of liquid aerosols such as hydrocarbons and water at this stage is preferable, if possible, to protect the dryer desiccant, since adsorption of such liquids shortens its life, and reduces its capacity for water and hydrocarbon vapors. Any droplets that remain as stable aerosols and mists are removed in part by the adsorbent of the desiccant dryer and the activated carbon of the oil vapor adsorber, and the remainder are removed in the bacterial retentive final filter.

The function of the adsorbent desiccant dryer is to produce low dewpoint air which will not condense water and thus foster the growth of bacteria in the conduits and pipes of the system or in itself contaminate product. 1SA-S7.3 *Quality Standard for Instrument Air* defines instrument quality air as having a dewpoint at pressure 10° C. less than local ambient. Heatless dryers are known, and are described in the Skarstrom U.S. Pat. No. 2,944,627, and in many subsequent patents. Such dryers normally have two chambers, each containing a bed of sorbent or desiccant, one of which is on-stream for drying while the other is off-stream for reactivation. A portion of the dry effluent is used to regenerate the spent desiccant bed at a lower pressure. The flow diagram for one-half cycle for adsorption and regeneration of the beds is shown in FIG. 1. In the systems as represented in FIG. 1, the wet gas enters the bottom of the lefthand chamber, passing upwardly through the desiccant, where it is dried to a low dewpoint, and then through the check valve to the dry air outlet. A small proportion of the dry gas is expanded, thereby reducing pressure, through the orifice between the chambers, and flows down through the righthand chamber, reactivating the desiccant at a lower pressure, and then is exhausted through the purge exhaust. At the end of the cycle shown in FIG. 1, the chambers are automatically switched, in the next half of the cycle the righthand chamber becoming the onstream chamber for drying, and the lefthand chamber being reactivated. Now the wet gas enters the bottom of the righthand chamber, passing upwardly through the desiccant, and then through the check valve to the dry air outlet, while a small percentage of the dry gas is expanded through the orifice between the chambers, and flows down through the lefthand chamber, reactivating the desiccant, and then passing out through the purge exhaust.

When at the end of the cycle the chambers are switched, the flow then returns to that shown in FIG. 1, and the entire cycle is repeated.

Such desiccant dryers can produce from −40° F. to −100° F. uniform dewpoint air, depending on the size of the desiccant bed and the cycling, far lower and more uniform dewpoints than obtainable at low operating cost with refrigeration-type or heat-reactivated type dryers. This means far less water in the effluent air per unit operating cost, and also increases the efficiency of oil vapor removal in the next component of the system, the oil vapor adsorber. The desiccant dryer also provides quantitative hydrocarbon vapor removal, to the extent that there is excess desiccant capacity. Some hydrocarbon aerosol droplets are removed at this stage.

By the time the air being processed has reached the activated carbon adsorber, the bulk of oil and water droplets, moisture vapor and most hydrocarbon vapors have been removed. Some hydrocarbon vapor, such as oil, remains, and it is such vapor that is removed nearly quantitatively by adsorption on the sorbent particles of the activated carbon adsorber. The adsorber is essentially a vessel containing a bed of activated carbon. Flow can be from either direction through the bed, but is preferably downwards, to prevent fluidizing the bed. With properly determined contact time, it is possible to remove substantially all hydrocarbon vapors (exclusive of methane and ethane), as confirmed by gas chromatography and total carbon analysis.

Flow of the air through two beds of particulate sorbents, first desiccant and second carbon, results in some pick-up of small particulate material, and this is removed in the next component of the system, the after-filter. This filter has a relatively coarse removal range, high area, high dirt holding capacity, and low initial clean pressure drop, thus providing long life protection in the system.

The final components to be removed are any remaining hydrocarbon aerosols, bacteria, and particles less than about 0.9 $\mu$m in largest dimension that pass through the after-filter. This is accomplished by using a filter having a fine enough pore size to screen out these particles by direct interception. Such filters accordingly have a maximum pore diameter not substantially in excess of 0.3 $\mu$m, and preferably below 0.3 $\mu$m. It can however to demonstrated by statistical analysis and also bacterial count that substantially all bacteria are removed by filters of the membrane type which have pores ranging as high as 1 $\mu$m, if the number of such pores is small (see the paper by David B. Pall delivered on June 12, 1978, before the 52nd Colloid and Surface Science Symposium, University of Tennessee, Knoxville, Tennessee).

Accordingly, the effluent from the air purification system is substantially free of hydrocarbon droplets, aerosols and vapor, moisture, particles and microorganisms, and consequently meets the proposed standards of paragraph 212.223 Compressed Air, of the *Federal Register* of June 1, 1976.

The air purification system shown in FIG. 1 is designed to obtain pharmaceutically-acceptable air from ambient compressed air as supplied from a conventional compressor set-up including an oil lubricated compressor A, then flows through an after cooler B for cooling the hot compressed air, where it is brought down to ambient temperature, and into the reservoir C, whence it is withdrawn as required and is then passed through the air purification system of the invention. From the reservoir the compressed air passes through the reverse flow coalescing filter D. This filter is provided with a sight glass E, and a drain valve F, for use when it is necessary to service the coalescer. Thence, the air passes directly to the air inlet of the heatless dryer G, flowing through whichever of the two tanks I, II is on-stream for adsorption, and then moves through the outlet from the desiccant dryer system to the oil and other hydrocarbon vapor adsorber H. The air then passes through an after-filter J, and finally through a bacterial-retentive filter K, after which it is conducted to the purified air outlet M from the air purification system.

The system is provided with oil aerosol indicators N, tapping the lines from the heatless dryer, the coalescer and the bacterial-retentive final filter, to ensure that oil droplets are quantitatively removed.

Pressure gauges O also are provided, to indicate the gas pressure in the two chambers I, II, as well as the purge effluent pressure of the heatless dryer. Controls P are provided to close and open the system inlet and system outlet lines.

Sampling ports Q sample the inlet air at the air intake to the system, so that this can be appraised, and the removal capability of the system adjusted accordingly, as well as the effluent from the heatless dryer, the air in the oil vapor adsorber, and the effluent air just before the system outlet, so as to make it possible to monitor the efficiency of the system at these stages, and make adjustments, if necessary.

The control panel R is provided with lights S indicating when the power is on or off, switching failure in the cycling of the heatless dryer, and which of the two chambers is on the drying portion of the cycle for that chamber.

The Oil and Water Coalescer:

When a filter sheet with pores smaller than the size of a droplet is placed across the flow stream, it will act as a sieve. By direct interception, if effectively stops and traps the droplet. When the droplets are smaller than 0.5 $\mu$m in size, they exhibit random movements, called Brownian motion, usually transverse to the flow path. The resultant motion of the droplet causes it to act in a manner similar to a droplet with an apparent diameter equal to the amplitude of the motion. Accordingly, a filter medium is effective in stopping particles small enough to pass through because of their larger apparent diameter as a result of Brownian movement. This mechanism of filtering out droplets is referred to as diffusion interception. A third mechanism is impaction, whereby the droplet directly impinges upon and is held by the filter body itself.

The coalescer takes advantage of all three mechanisms.

The coalescer comprises a first stage coalescer, in which the entrained liquid droplets are coalesced into droplets sufficiently large to be affected by gravity, and in which a proportion of the thus coalesced oil and water drops fall to the bottom of the coalescer, and a second stage coalescer or stripper in which most of the remaining portions of the partially condensed droplets are further coalesced, and drain to the bottom of the coalescer.

The liquid collected at the bottom is drained off, and in the case of lubricating oil may, for example, be returned to the oil sump of the compressor.

The first stage coalescer is a nonwoven fibrous mat or layer, if desired supported on a substrate, of relatively low density, and a relatively high porosity; porosity being defined as the percentage of voids.

Any fibrous material inert to oil can be used in the nonwoven fibrous mat or layer. Suitable fibrous materials include glass, quartz, ceramic, titanium dioxide, alumina, polyvinyl chloride, polyethylene, polypropylene, polyacrylonitrile, polyester, polyvinylidene chloride, regenerated cellulose, asbestos, cellulose acetate, resin-impregnated cotton, and polytetrafluoroethylene.

The fibers are sufficiently long so that they are capable of forming a coherent nonwoven mat or layer. Neither their length nor the diameter is critical, but for efficient coalescing action it is important that the nonwoven mat offer a high surface area and density, and for this purpose fine fibers are better than coarse fibers. Ordinarily, fiber diameters are within the range from about 0.5 to about 5 microns.

The density of a nonwoven mat is controlled by confining the mat between rigid facing sheets. The rigidity of the sheets must be adequate to retain the nonwoven mat under the differential gas pressures that may be encountered across the layer without appreciable distortion or rupture. The density of the layer should in general be within the range from about 0.05 to about 0.5 g/cc and preferably from about 0.2 to about 0.4 g/cc. As the facing sheets, sintered metal particle sheets; woven plastic or metal wire mesh, rolled and compressed and also sinter-bonded, if desired; perforate metal and plastic sheets; and resin-impregnated foraminous fibrous sheets can be used.

Since the fibrous layer is confined between facing sheets, it is not necessary that the fibers of the layer be bonded together. In fact, in a long fibered medium, if no binder is present, the porosity of the layer may be greater, and consequently, the pressure drop across the layer is less. It is desirable in order to maintain a high efficiency of separation of the entrained oil droplets to hold the pressure drop across the coalescer layer to as low as value as possible.

However, if short fibers are used, improved fiber retention and reduced compressibility can be obtained by bonding the fibers with a synthetic resin. Phenol-formaldehyde resins, urea-formaldehyde resins, melamine-formaldehyde resins, epoxy resins and others are quite satisfactory bonding agents. The bonding technique is conventional, and need not be further described, except, of course, to note that the amount of resin is less than will reduce unduly the porosity of the mat. Just enough resin should be used to coat the fibers and ensure bonding at their points of contact. The amount is readily ascertained by simple calculation of the surface area of single fibers of any given diameter and length. From 3% to 50% resin by weight is usually adequate for 0.1 to 2 micron diameter fibers.

A preferred method of making coalescer mats is to lay down a slurry of the fibers suspended in water of controlled pH on a cloth supported on the mesh of a Fourdrinier or paper making machine. A vacuum can be applied to condense the fibers to a mat on a cloth backing, which is then removed from the mesh screen support. The fibers can be similarly deposited from a suspension in air.

The second stage coalescer or stripper is of a porous sheet material which is coarser than the primary coalescer, but which is of a pore size such that the coalesced oil and water droplets are incapable of passing through the pores or interstices thereof, while the gas passes through freely. As the stripper sheet, a porous open-cell polyurethane foam can be used, having a porosity within the range from about 50 to about 150 pores per square inch, and having an average pore diameter within the range from about 0.005 to about 0.02 inch, and a voids volume preferably in excess of 80%.

The polyurethane foam can be made of any polyurethane resin which is not deteriorated by contact with oil. Any polymer of a diisocyanate and a glycol can be used, including aliphatic diisocyanates and aliphatic glycols, aromatic diisocyanates and aliphatic glycols, aliphatic diisocyanates and aromatic glycols, aromatic diisocyanates and aromatic glycols, cycloaliphatic diisocyanates and aliphatic glycols, aliphatic diisocyanates and cycloaliphatic glycols, and any mixtures thereof, in any desired proportions.

Also useful are porous fibrous mats or sheets of synthetic or natural organic fibers such as coarse fiber mat, or a mat of polypropylene fibers can be used as a stripper, provided its pore size and voids volume is in a similar range.

Particularly useful second stage coalescer or strippers are filter media having one or several microporous layers as distinct strata and made of fibrous material laid down on a substrate from a slurry thereof. Such materials are described in U.S. Pat. No. 3,238,056 dated Mar. 1, 1966 to David B. Pall and Cyril Keedwell; No. 3,246,767 dated Apr. 19, 1966 to David B. Pall and Cyril Keedwell; No. 3,353,682 dated Nov. 21, 1967 to David B. Pall and Cyril Keedwell; No. 3,573,158 dated Mar. 30, 1971 to David B. Pall and Cyril Keedwell, and No. 3,407,252 dated Oct. 22, 1968 and No. 3,591,010 dated July 6, 1971 to David B. Pall and Cyril Keedwell.

The microporous fibrous layer can be self-supporting or supported on the substrate on which the layer is laid down. The layers can be combined in multilayered laminates or composites, of which at least one layer and preferably each layer is microporous, and of a sufficiently small pore size to quantitatively remove bacteria. Such microporous sheet material is characterized by a voids volume in excess of 75%, obtained by selection of the particulate material of which the microporous layer is composed. The particulate material comprises fibrous material in an amount of at least 5% and preferably of at least 15% up to 100% and optionally nonfibrous particulate material in an amount from 0 up to 85%. Details on the formation of these layers will be found in the patents referred to.

Fibrous material is preferred as the particulate material, because of its versatility, greater ease of deposition, and greater strength-imparting properties, and because fibers can be oriented by liquid flow or absence of liquid flow so as to be deposited in a plane approximately parallel to the plane of the layer. A great variety of diameters of fibers are available, thus making it possible to achieve a very large assortment of mixtures of different diameter fibers, for making fibrous material of any porosity, and such fibers can be made of any length, within the stated range, so as to take advantage of the greater cohesiveness of a layer of long fibers, as compared to granular material layers. Typical fibrous materials include glass and quartz, ceramics, asbestos, potassium titanate, colloidal aluminum oxide ("Baymal"), aluminum silicate, silicon carbide whiskers, mineral wool, regenerated cellulose, microcrystalline cellulose, polystyrene, polyvinyl chloride, polyvinylidene chloride, polyacrylonitrile, polyethylene, polypropylene, rubber, polymers of terepthalic acid and ethylene glycol, polyamides, casein fibers, zein fibers, cellulose acetate, viscose rayon, hemp, jute, line, cotton, silk, wool, mohair, paper, metallic fibers such as iron, copper, aluminum, stainless steel, brass, Monel, silver and titanium, and clays with acicular lath-like or needle-like particles, such as the montmorillonite, sepiolite, palygorskite, and attapulgite clays of this type.

Most of the oil and water mist incident on the primary coalescer is condensed to larger droplets, which flow by gravity to the bottom of the coalescer, and thence into the sump; however, a small proportion, usually between about 2 and about 15%, is instead entrained in the air leaving the coalescer, in the form of relatively large (e.g. 0.2 inch diameter or larger) droplets. These collect on the stripper, if the stripper is placed at an angle to the horizontal, the coalesced oil and water runs down the stripper by gravity, to collect at the base, and drains off. The oil can be returned to the oil reservoir or sump, after phase-separation of any water layer.

It is frequently convenient to arrange the coalescer and stripper elements concentrically, each being in the form of a cylinder or other closed configuration, one within the other. To provide for a greater surface area within a confined space, the coalescer element can be folded in an undulating or corrugated configuration. The coalescer can be the outer of two elements, in such a concentric arrangement, flow being from outside in, with the water and oil being collected at the center from the surface stripper element, draining down by gravity, while the air discharge is up. However, it is usually preferable to use the reverse arrangement, with flow from inside to out, as the velocity of the air leaving the stripper is lower, leading to a lower tendency to entrain droplets from the stripper. In order to obtain greater surface area and volume it is desirable to arrange the coalescer and stripper elements so that the coalescer element is the innermost and the stripper element the outermost, and flow is from inside out, through the demister assembly.

A concentric arrangement is not essential, however, although it is convenient for many uses. The coalescer and stripper elements can also be arranged as flat or corrugated sheets, with flow proceeding from one side to the other of the composite, which is arranged in-line.

Figure 3:
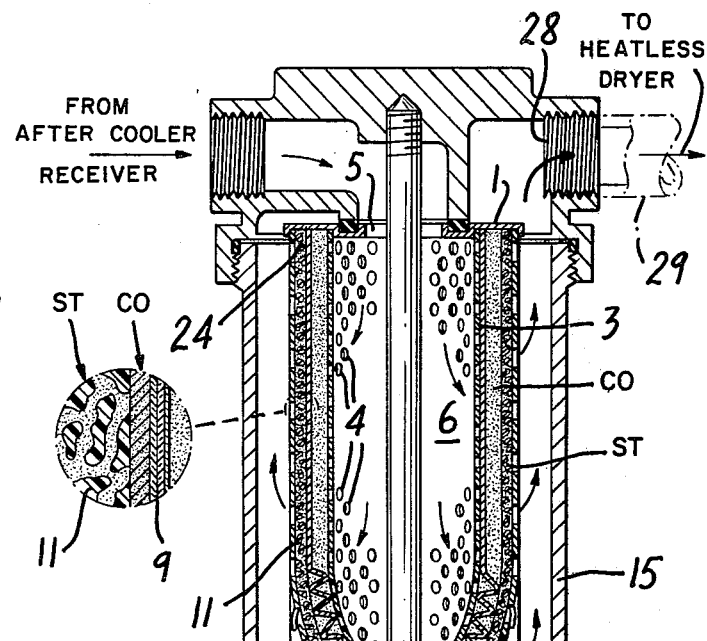

In a preferred embodiment of coalescer, and that shown in FIGS. 1 and 3, the coalescer has a first stage coalescer composed of layers of extremely fine glass fibers, integrally epoxy-bonded together to form a strong sheet having a voids volume of approximately 90%, with fine pores less than 0.1 $\mu m$ in diameter. This coalescer effectively traps and coalesces small liquid droplets, as small as 0.3 $\mu m$ in diameter, and is not attacked by oil or water. 0.3 $\mu m$ droplets are the most difficult size to remove. Droplets smaller than 0.3 $\mu m$ exhibit sufficient Brownian motion to behave as droplets greater than 0.3 $\mu m$ and are removed via indirect interception.

This sheet is pleated with a layer of epoxy-bonded cellulose fiber support and drainage member, and formed into a high-area corrugated cylindrical configuration, which is then wrapped in an open-celled polyurethane foam sheet, but a polypropylene fibrous mat can also be used. This cylinder is assembled over a rigid support core, and placed inside rigid external support, and capped off with metal or plastic end caps epoxy-bonded to the ends of the cylinder. The core can be of plated steel, stainless steel, or any other rigid metal or plastic material.

The coalescer filter shown in FIGS. 1 and 3 is in cylindrical form, within a housing 15, with the coalescer CO and stripper ST components being arranged concentrically, the several concentric cylinders thereof confined between and bonded to end caps 1, 2. The layers are supported upon an inner perforated convoluted plated steel or stainless steel core 3, a perforated sheet formed in a cylinder and having a plurality of relatively large apertures 4. The end cap 2 is blind, but the end cap 1, also of plated steel, has a central aperture 5, serving as an inlet for oil-laden air into the central space 6 of the assembly, within the metal core 3.

The coalescer filter CO is innermost, supported upon the core 3, and the stripper ST is outermost, supported within the outer sheath 7 with both layers being confined under compression between the core 3 and the sheath 7. The sheath 7 is a perforated plated steel or stainless steel cage.

The coalescer filter material is a corrugated composite of four layers: an outer sheet 8 of epoxy-impregnated cellulose paper. 0.020 inch thick; two layers of nonwoven epoxy-bonded fibrous mat 9 of glass fibers approximately 0.012 inch in diameter, and an innermost layer of cellulose paper 0.002 inch thick.

The stripper ST is wrapped around the coalescer filter CO, and comprises a layer of ¼ inch thick foamed polyurethane sheet 11 or polypropylene fibrous mat, not corrugated. The foam or fibrous mat layer is in close juxtaposition to the outer sheath 7, in order to obtain as compact an assembly as possible.

Each of the concentric cylindrical layers CO and ST is bonded to the end caps 1, 2 at each end by the potting compound 24 such as an epoxy resin in a leak-tight seal, thus ensuring that all flow entering the center 6 of the assembly through the inlet 5 of end cap 2 must pass through the several layers, in order to emerge through the sheath 7.

In operation, liquid-laden air enters the assembly through the inlet 5 of end cap 2. It then proceeds through the core 3, thus entering the coalescer CO, and passes through mat 9. In the course of passing through the coalescer mat 9, the entrained liquid droplets are coalesced to form larger droplets, which grow in size until the balls of the liquid settle to the bottom of the element by gravity. A small proportion of the liquid is entrained as relatively coarse drops. Because of their relatively large size, these drops are collected within the polyurethane foam or polypropylene fibrous mat, coalescing into still larger drops, which flow down by gravity to the bottom of the element, and thence flow over the lip 21 of the end cap 2 into the sump 25 at the base of the housing.

The housing 15 is provided with an outlet 26, which leads to the oil line 27, so that the oil collecting in the annular space 8 and sump 25 can be withdrawn through the outlet 26 via the oil line 27.

The air passes through the polyurethane foam or polypropylene mat layer 11, now substantially free from oil and water droplets, and escapes through the outer sheath 7, and then through outlet 28 of the housing, whence it is conducted via the air line 29 to the heatless dryer.

The Adsorbent or Desiccant Dryer

Desiccant dryers are available of two general types, a heat-reactivatable type, in which heat is applied to regenerate the spent desiccant at the conclusion of the drying cycle, and a heatless dryer, in which heat is not applied to regenerate the spent desiccant at the conclusion of the drying cycle, but which relies upon the use of a purge flow of dry gas, usually effluent gas from the bed on the drying cycle which is passed through the spent bed at a lower pressure with rapid cycling to conserve the heat of adsorption to aid in the regeneration of the spent bed. The heat-reactivated desiccant dryers can be employed in the air purification systems of the invention, but are less preferable because their long drying cycle inhibits coadsorption of water and hydrocarbon vapors, necessary to provide reasonable life of the oil vapor removal units activated carbon. The heatless dryers are accordingly preferred.

The heatless dryer can be operated with fixed time drying and regenerating cycles, usually equal in duration, with the length of the cycles being fixed according to the volume of desiccant available, and the moisture and hydrocarbon vapor content of the influent air. The time of the cycle is, in this event, fixed at much less time than might be permitted, in order to ensure that the moisture content of the effluent gas will always meet the system requirements.

If desired, the heatless dryer can also employ an automatic cycle control, as described in U.S. Pat. No. 3,448,561, patented June 10, 1969, to Seibert and Verrando. This process and apparatus make it possible effectively to utilize the moisture capacity of the desiccant bed by providing for regeneration thereof only when the moisture load on the bed requires it, and thus obtain optimum efficiency in use. During each adsorption cycle, the sorbent can be brought to the limiting moisture capacity at which regeneration can be effected under the available regenerating conditions, whether these be with or without the application of heat, and with or without the application of a reduced pressure.

This is made possible by detecting the advance of the moisture front within the bed as evidenced by the moisture content of the gas being dried, and halting the drying cycle whenever the front has reached a predetermined point in the bed short of breaking out of the bed. This can be done automatically by providing in the desiccant bed means for sensing the moisture content of the gas being dried, and means responsive to moisture content to halt the drying cycle whenever a predetermined moisture content in the gas being dried is reached. Further details on this process and system will be found in U.S. Pat. No. 3,448,561, the disclosure of which is hereby incorporated by reference.

While the heatless dryer can be composed of one desiccant bed, the preferred heatless dryer employs a pair of desiccant beds, disposed in appropriate vessels, which are connected to the lines for reception of influent gas to be dried, and delivery of effluent dried gas.

The drying apparatus can also include a check valve or throttling valve for the purpose of reducing pressure during regeneration, and multiple channel valves for cycling the flow of influent gas between the beds and for receiving the flow of effluent gas therefrom. In addition, a metering or throttling valve can be included to divert a portion of the dried effluent gas as purge in counter-flow through the bed being regenerated.

The heatless dryer can be used with any type of sorbent adapted to adsorb moisture from gases. Activated alumina is preferred, since it provides excellent overall moisture and hydrocarbon removal, characteristics desired in this system. Activated carbon, alumina, silica gel, magnesia, various metal oxides, clays, fuller's earth, bone char, and Mobilbeads, and like moisture-adsorbing compounds can be used as the desiccant. Preferably, the desiccant is different from the sorbent used in the adsorber which follows the dryer in sequence.

Molecular sieves also can be used, since in many cases these have moisture-removing properties. This class of materials includes zeolites, both naturally-occurring and synthetic, the pores in which may vary in diameter from the order of several angstrom units to from 12 to 15 Å or more. Chabasite and analcite are representative natural zeolites that can be used. Synthetic zeolites that can be used include those described in U.S. Pat. Nos. 2,442,191 and 2,306,610. All of these materials are well known as desiccants, and detailed descriptions thereof will be found in the literature.

The dryer described and shown in the drawings is adapted for upflow adsorption and downflow regeneration flow, but it can also be operated with downflow adsorption and upflow regeneration flow. In purge flow regeneration, the purge passes in counterflow to the wet gas influent. This as is well known, is the most efficient way of utilizing a desiccant bed. As a wet gas process through a desiccant bed in one direction, the moisture content of the desiccant progressivly decreases, and normally the least amount of moisture will have been adsorbed at the outlet end of the bed. It is consequently only sound engineering practice to introduce the regenerating purge gas from the outlet end, so as to avoid driving moisture from the wetter part of the bed into the drier part of the bed, and thus lengthen the regeneration cycle time required. If the purge flow be introduced at the outlet end, then the moisture present there, although it may be in a small amount, will be removed by the purge flow and brought towards the wetter end of the bed. Thus, the bed is progressively regenerated from the outlet end, and all the moisture is carried for the least possible distance through the bed before it emerges at the inlet end.

Nonetheless, for some purposes, it may be desirable to run the purge flow in the same direction as the influent flow. It is possible to carry the moisture content of the desiccant to a very high level, much higher than is normally feasible. The protecting action of a humidity sensing element is utilized, as in U.S. Pat. No. 3,448,561, which makes it possible to cut off flow at a time more precisely gauged to moisture level than has heretofore been possible. Consequently, in many cases if the bed is brought nearly to the saturation point throughout, it will make little difference if the purge flow enters at the influent end or at the outlet end, and the invention contemplates both types of operation, although of course counterflow regeneration is preferred in most cases.

Figure 2:
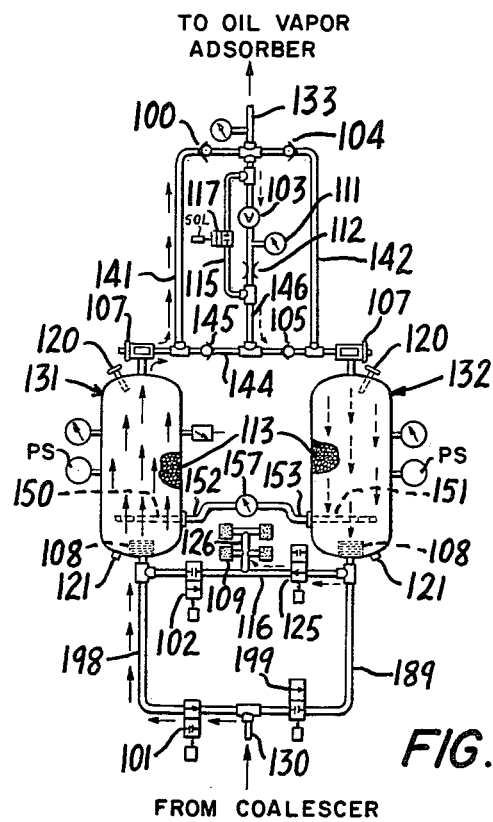

The dryer shown in FIG. 2 is composed of two tanks, 131 and 132, fitted with suitable line connections for delivering wet gas influent and dry gas effluent to and from each tank, and with desiccant fill and drain ports 120 and 121, respectively. The desiccant 113 is supported on perforated cylindrical supports 108 in each tank. Control of wet gas influent flow from inlet line 130 is by valves 101 and 199, which direct the flow of influent gas either to line 198 or to line 189, and thence to the bottom of the tanks 131, 132.

Dry gas effluent leaves the tanks via one of lines 141 or 142, both of which are connected to the dry gas outlet 133. In each line is a cleanable filter of sintered stainless steel wire mesh 107, and a check valve 100, 104.

A cross line 144 bridges the outlet lines 141, 142, and is fitted with two check valves 105, 145 on either side of a parallel line 146 extending to the outlet line 133. In line 146 is a pressure-reducing orifice 112, beyond which pressure is reduced to atmospheric, when purge exhaust valves 102 or 125 are open, and purge adjusting valve 103 for metering flow through line 146. This controls the volume of purge flow bled off the effluent gas for regeneration of the spent tank, which is read off from purge flow indicator 111.

A by-pass line 115 by-passes the purge flow orifice 112 and adjusting valve 103, for repressurization, controlled by valve 117. Another line 116 extends between lines 198 and 189, and is fitted with purge exhaust valves 102 and 125, respectively, which vent purge to the atmosphere when open, through the exhaust mufflers 109, in line 126.

At points approximately six inches from the inlet of each tank are a pair of humidity sensing probes 150, 151. Moisture-laden gas is conveyed via lines 152, 153 to a humidity sensor 157, which detects the moisture level therein, and responds thereto when a predetermined moisture level is reached, and controls the timer, which controls operation of the valves 101, 199 and also the purge exhaust valves 102, 125 and repressurization valve 117.

If the lefthand tank is on the drying cycle, and the righthand tank on the regenerating cycle as shown in FIG. 2, then the operation of the dryer proceeds as follows: wet gas influent at, for example, 100 p.s.i.g., and a flow rate of 305 s.c.f.m., saturated at 80° F., enters through the inlet 130 into the line 198, passes the valve 101, and enters the bottom of the first tank 131, and thence upwardly through the bed of desiccant 113 therein, for example, silica gel, past the humidity sensing probe 150, and thence through the filter 107, line 141 (check valve 145 preventing entry into line 144), and through check valve 100 to the dry gas outlet line 133. Effluent gas is delivered there at 100 p.s.i.g. and 265 s.c.f.m. dewpoint −40° F. Check valve 104 prevents entry of dry gas into line 142. The remainder of the dry gas effluent, 40 s.c.f.m., in this example, is bled off through the line 146 from the end of line 141 at the outlet and conducted past valve 103 and orifice 112, where its pressure is reduced to atmospheric, and then through line 144 to the top of the second tank 132, which is on the regeneration cycle. Purge flow passes downwardly through the desiccant bed 113, and emerges at the bottom into line 116, and thence passes through purge exhaust valve 125 to line 126 and mufflers 109, where it is vented to the atmosphere.

Since the time that each bed will be on the drying cycle is normally much greater than the length of time required to regenerate the spent bed, purge exhaust valves 102, 125 are timed so as to be actuated only for the time necessary to complete regeneration of the desiccant. When this time has elapsed, they are automatically shut off, and repressurizing valve 117 is automatically opened. This is done by a timer.

This cycle continues until the humidity sensor 157 via probe 150 has detected the predetermined moisture level in the gas in the tank 131, whereupon the timer is reenergized, and first closes valve 117, then opens valve 199, and then closes valve 101, and then opens valve 102, so that wet gas influent entering through inlet 130 passes through line 189 to tank 132, while dry gas effluent can now pass from the top of the tank 132 to the dry gas delivery line 133, and entry of dry gas into lines 141 and 144 from line 142 is prevented. The flow of purge gas in the cross-line 144 is now reversed, and purge flows in line 144 through valve 145 to the top of tank 131 which is on the regeneration cycle, and thence downwardly through the bed to the line 198, and thence through valve 102 and line 116, line 126 and mufflers 109, where it is vented to the atmosphere. This cycle continues until the predetermined regeneration time cycle is completed, whereupon the timer closes purge exhaust valve 102 and opens repressurizing valve 117 to repressurize tank 131. The system continues with tank 132 on the drying cycle until the humidity sensor 157 via probe 151 in tank 132 senses the predetermined moisture level in the gas in this bed, whereupon the timer is reenergized, the valves reversed, and the cycle begun again.

Usually, the drying cycle is carried out with gas at a superatmospheric pressure, of the order of 15 to 350 p.s.i.g. The orifice 112 in the cross-line 146 in combination with the purge exhaust valves 102 and 125 ensures that the regeneration cycle is carried out at a pressure considerably reduced from that at which the adsorption cycle is effected.

The drawing shows an upflow adsorption-downflow regeneration flow dryer. A downflow adsorption-upflow regeneration flow dryer, operating in a similar manner as above, will provide the desired effluent if properly sized for desiccant volume.

To ensure regeneration of the spent bed during the regenerating cycle, the time allotted by the timer and the volume of purge flow are adjusted according to the volume of desiccant, and the pressure at which the adsorption is effected, to ensure that regeneration can be complete within the allotted cycle time. Heatless dryers operate under equilibrium conditions, and the equilibrium conditions must be maintained under all of the conditions to which the dryer may be subjected in use.

The Activated Sorbent Adsorber

Oil and other hydrocarbon vapor and oil and other hydrocarbon droplets smaller than about 0.01 micron in diameter not adsorbed in the desiccant dryer are adsorbed on a bed of particulate activated sorbent, such as activated carbon or activated alumina. In the event of desiccant dryer malfunction, due for example to cycling failure or sorbent life extinction, the activated carbon adsorber will adsorb moisture and provide dewpoint control for short periods of time, the time being dependent on the amount of water and hydrocarbon vapor in the influent from the dryer. Any activatable sorbent can be used, including, for example, any of the sorbents/desiccants referred to in the preceding discussion of the heatless desiccant dryer.

The particle size and volume of the particulate adsorbent bed provided is necessarily determined in part by the proportion of oil and other hydrocarbon vapor to be adsorbed. Time is required for the sorption process, and inasmuch as flow rate is a function of other components of the system, the volume of sorbent should be sufficient to allow the required contact time. Longer contact times of course require larger vessels, and larger volumes of sorbent.

Figure 4:
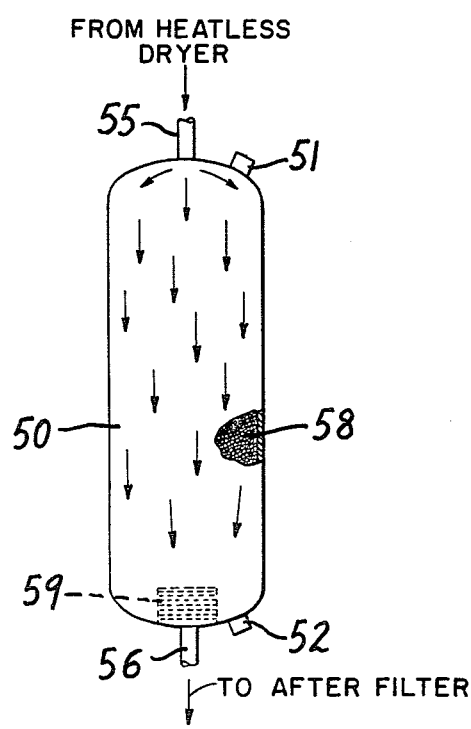

The hydrocarbon vapor adsorber shown in FIG. 4 has a cylindrical tank 50 arranged vertically, with fill ports and drain ports 51, 52, respectively, an air inlet 55, and an air outlet 56 at the top and bottom of the tank, respectively. The bed of particulate sorbent 58 is supported on a coarse perforated plate cylinder 59, as in the desiccant dryer of FIG. 2. The sorbent is preferably activated carbon or activated alumina. While the tank shown provides for downward flow of air through the sorbent bed, which permits higher flow rates, upward flow can also be used. In this case, lower flow rates are required to prevent fluidization of the bed, and a top screen should also be furnished, to compress the bed and prevent bed breathing, so as to limit the dusting problem. A gas sampling probe may be provided before the outlet to provide sufficient notice of impending sorbent bed exhaustion to allow for time to regenerate or replace the spent sorbent charge before delivery of contaminated effluent.

The compressed air from the carbon adsorber, now essentially free of both oil and water droplets and oil and water vapor, enters the after-filter, to remove any particulate material added to the air in the course of passage through the particulate sorbent beds of the dryer system and the adsorber system.

The After-Filter

The after-filter is composed of a plurality of fibrous filter sheets of different pore size, having a nominal removal rating for liquids within the range from about 0.5 to about 50 μm, and an absolute rating from 3 to 30 μm, and for gases within the range from about 0.1 to about 25 μm (nominal) and from 1.5 to 40 μm absolute, arranged in sequence of fluid flow therethrough according to decreasing pore size, preferably of nonwoven fibrous mats or sheets free from synthetic resin or binders or other additions. While preferably of cellulosic or polypropylene fibers any of the fibrous materials referred to as suitable for use in the coalescing filter can be used. The sheets are formed in a concentric corrugated tubular configuration, for fluid flow therethrough across the tube from one side to the other side, with at least one foraminous relatively rigid support and drainage member in corrugated supporting juxtaposition to the filter tube.

The support and drainage member provides a sufficient rigidity to the filter sheets to avoid the necessity of resin or binder impregnation of the filter sheets, and also makes it possible to use rather thin sheets. The use of corrugated filter sheets provides a greater surface area, and hence a higher dirt capacity, within a given volume. Adequate rigidity is obtained to prevent layover. By using appropriate layers, graded from coarse to fine, in sequence of fluid flow, the air-borne particulate solid material from the preceding sorbent beds and any other solid contaminants are screened out according to size, and filter tubes with a higher dirt capacity and a longer surface life, as well as a better removal rating, and a higher efficiency, can be provided.

The foraminous relatively rigid support and drainage members have a rigidity that is higher than the filter sheet, and sufficient strength to withstand encountered differential fluid pressure across the filter tube.

Suitable foraminous external and interior supports can be made of metal or plastic, and can be, for example, in the form of perforated sheets or plates, or woven or nonwoven or extruded netting, made of plastic filaments or extrusions. The preferred foraminous sheets are made of extruded netting of synthetic resinous material. Any thermoplastic synthetic resinous material can be employed, such as polyethylene, polypropylene, polybutylene, polystyrene, polyamide, cellulose acetate, ethyl cellulose, cellulose acetate butyrate, copolymers of vinyl chloride and vinyl chloride and vinyl acetate, polyvinyl chloride, polyvinylidene chloride, vinylidene chloride-vinyl chloride copolymers, polyvinyl butyral, polytrifluorochloroethylene, polymethyl methacrylate, and synthetic rubbers.

Extruded plastic netting is available in a variety of patterns. In some, the plastic has an open weave pattern, with the extruded netting links in one direction having the same diameter as the extruded links in the other. Others have the extruded links wider in one direction than in another, forming ribs extending lengthwise, or crosswise, or circumferentially, of the netting. Netting generally is preferred in which the extruded links are of uniform diameter, or, if one is of larger diameter than the other, the larger diameter extrusions run circumferentially of the netting, so as to minimize blockage of the convolutions or corrugations of a corrugated filter element. Extruded nettings also are available having diagonal patterns with the openings tetragonal, and in others cross-diagonals are bisected by longitudinal extrusions forming triangular openings. Any of these can be used.

Nonwoven materials, called "spun-bonded", can be prepared by laydown of extruded thermoplastic synthetic resin filaments while still soft in the form of a nonwoven mat. The soft fibers adhere to one another, and when cooled form an integral mass of nonwoven filamentary structure. This technique is applicable to glass fibers, to polyamides, and to other thermoplastic fibers.

Nettings also are formed from extruded thermoplastic resin sheet, which is embossed during or after extrusion and then stretched to open holes in the embossed areas, resulting in the formation of a netting in sheet form.

Perforated sheet also can be used. In this case, elongated perforations can be punched or machined in the sheet or formed by application of heat localized to the areas to be perforated.

Spun-bonded nonwovens can also be prepared by laying down two types of fibers as a nonwoven mat, one fiber being lower melting and present in small proportion. When the web is heated to above the softening point of the one fiber, it becomes firmly bonded. This technique is applied commercially to polyester fibers.

In order to enclose the filter element in a tight external protective sheath, it is advantageous to employ extruded netting (tubular, in the case of a tubular or cylindrical filter element) having a diameter slightly less than the external diameter of the element. The tubular netting is heat softened and expanded, the filter element inserted, and the tubular netting then allowed to cool and harden, and at the same time shrink to embrace the filter element in a snug fit, providing excellent support and rigidity to the element.

If thermoplastic extruded, woven or nonwoven netting is employed as the external and internal support, thermoplastic material also can be used as the end caps, and for this purpose it is advantageous to form the end caps and the netting of the same plastic material. Polypropylene and polyethylene are preferred, because of their inertness and durability, as well as high tensile strength and rigidity, but many other thermoplastic materials are suitable.

Two or more filter sheets placed in contact with each other are advantageous because occasional random defects may be present in the sheets. By placing two sheets face to face, the probability of two defects being superimposed on each other becomes remotely small.

Support and drainage members such as cover sheets can then be put on one or both sides of the composite. The composite is then corrugated, to the desired number and depth of corrugations, formed into a tubular configuration, in a manner such that the pore size of the juxtaposed filter sheets is in decreasing order in the intended direction of fluid flow through the composite, from inside to outside or from outside to inside of the filter tube, and the ends lapped over and bonded together in a side seam seal. In this way, the corrugations of the support and drainage members match the corrugations of the filter sheet, and these sheets are in corrugated supporting juxtaposition to the filter sheets.

The open ends of the filter cartridge thus obtained are closed off by end caps, of which at least one has an aperture therethrough for access of fluid to the open interior of the filter cartridge.

The end caps can be bonded to the filter element by application of an adhesive, or by application of heat and pressure, or a solvent if the binder in the filter sheet is thermoplastic or solvent-soluble, or if the end caps are thermoplastic, and/or solvent-soluble. A suitable bonding method in the case of thermoplastic end caps is described in U.S. Pat. No. 3,457,339, dated July 22, 1969 to D. B. Pall, et al, the disclosure of which is hereby incorporated by reference. In this procedure, the end cap interior is softened by rapid application of heat, so as to obtain softening before the exterior of the end cap has been softened, to prevent the end cap from being distorted, or lose its shape. Thermoplastic materials that can be used and the temperatures which can be employed in obtaining the bonding are given in the Table at column 6 of the patent.

A particularly preferred after-filter has corrugated filter sheets of nonwoven polypropylene fibrous mat, polypropylene end caps, a foraminous polypropylene internal core, and an external protective sleeve of extruded polypropylene netting, all adhered together by melt-bonding. The corrugated filter sheets are in the form of a cylinder, with the longitudinal seam sealed by melt-bonding the sheet edges together. The resulting filter cartridge is integrated in one piece, and is extremely rugged and durable.

A preferred paper filter cartridge is described in U.S. Pat. No. 4,033,881, patented July 5, 1977, to David B. Pall, the disclosure of which is hereby incorporated by reference.

Figure 5:
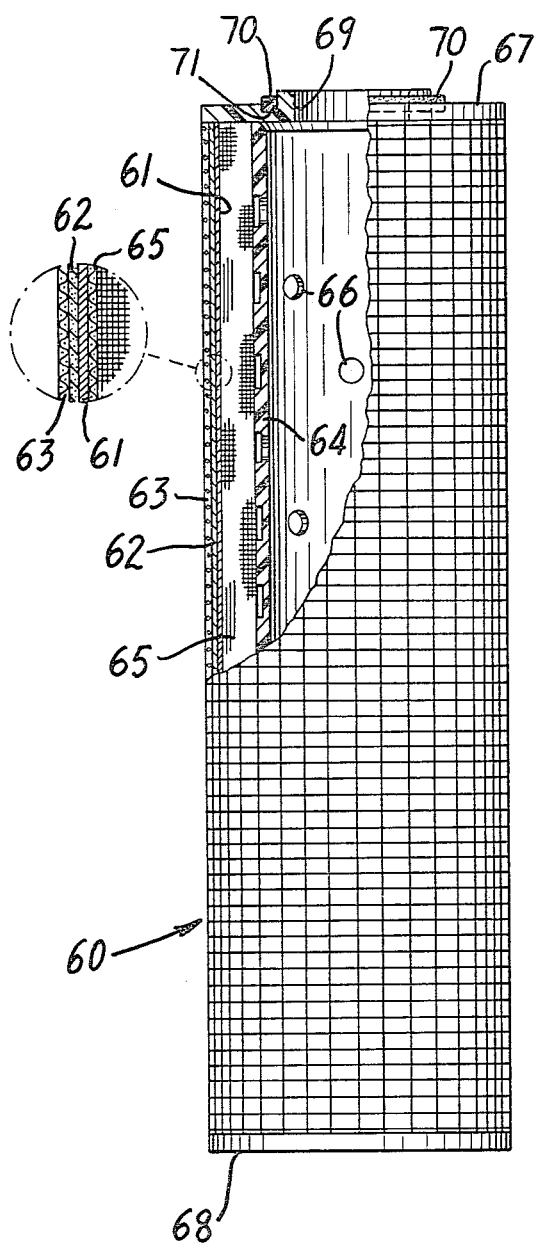

The details of the after-filter are shown in FIG. 5.

The after-filter shown in FIG. 5 is composed of two filter sheet materials 61, 62, of which the relatively coarser porous paper sheet 2 (Type A) is on the outside, and a finer porous paper sheet 1 (Type B) on the inside.

The sheet designated as Type A is a low density regenerated cellulose bonded hemp filter sheet having the following properties:

| Basic Weight | 4.5 per sq. ft. |
| Thickness | 0.009 inch |
| Density, g/cc | 0.21 |

Liquid displacement and glass bead penetration methods determine pore size to be:

| Average pore size | 40 μM |
| Maximum particle passed | 90 μM |

The second sheet, designated as Type B, is hemp filter sheet similar to the above, but at a higher density:

| Basic weight | 4.5 per sq. ft. |
| Thickness | 0.007 inch |
| Density, g/cc | 0.27 inch | of a pore size determined to be:

| Average | 28 μM |
| Maximum particle passed | 65 μM |

The two sheets were cut to 9½ inches wide, and assembled with inner and outer layers 65, 63 of 18×14×0.009 inch polypropylene woven mesh on either side. The composite was corrugated with 85 corrugations, each 0.45 inch deep.

The arrangement of the composite placed the Type A sheet outermost and the Type B sheet innermost, so that flow was from out to in, and through the coarser layer first.

The resulting filter sheet composite had the following characteristics:

| Maximum particle passed | 55 μM |
| Dirt capacity to 50 psia as determined by passing a suspension of AC fine test dust in water at 10 liters/minute: | 185 g |

The composite was folded to form a cylinder 60, with the ends lapped over and sealed, and slipped over a foraminous cylindrical polypropylene core 64 provided with apertures 66 for flow into the open interior of the core, and the ends of the cylinder were capped by end caps 67, 68 of polypropylene resin.

The end caps were sealed by fusion to the ends of the filter cylinder 60, closing off the interior from the exterior of the filter element. Fluid flow can thus be from the outside to the interior of the filter element, via sheets 62, 61, in that order, since interior and exterior are completely separated by the filter element, sealed off by the end caps 67, 68. The end cap 67 has a central aperture 69 with a central groove 71 and a sealing gasket 70 in the groove.

In place of paper sheet, nonwoven polypropylene fibrous mats can be used. Then, the longitudinal seam of the filter cylinder is sealed by melt-bonding, and the filter cylinder sealed to the end caps and to the core, and to a protective external sleeve, to make an integral filter cartridge.

The compressed air from the after-filter contains as the only remaining solid particulate material bacteria and other microorganisms, and solid particulate material of the same size range of the microorganisms, as well as small quantities of hydrocarbon aerosols such as oil. These contaminants are removed in the bacterial-retentive final filter.

The Bacterial-Retentive Final Filter

The bacterial-retentive final filter comprises a microporous filter sheet having a high voids volume, and a pore size of less than 3 μm and preferably less than 0.3 μm, small enough to quantitatively remove all bacteria, fungi, and similar microorganisms in the flow stream passing through it.

Suitable microporous sheet materials include resin membranes having ultrafine or micropores and no pores beyond the permissible maximum of 3 μm. Microporous membrane filters can be made of cellulose derivatives or synthetic resins, including, for example, those described in U.S. Pat. No. 1,421,341 to Zsigmondy; No. 1,693,890 and No. 1,720,670 to Duclaux; No. 2,783,894 to Dovell et al; No. 2,864,777 to Robinson; and No. 2,944,017 to Cotton.

Also useful are the synthetic resin membrane filters described in U.S. Pat. No. 3,615,024 dated Aug. 26, 1968 to Michaels; No. 4,032,309 dated June 28, 1977 to Salemme; No. 3,709,774 dated May 13, 1970 to Kimura; No. 2,783,894 dated Mar. 5, 1957 to Lovell; No. 3,408,315 dated Oct. 29, 1968 to Paine; No. 3,746,668 dated Dec. 27, 1971 to Hiratsuka et al; No. 3,980,605 dated Sept. 14, 1976 to Steigelman et al; and No.

3,901,810 dated Aug. 26, 1975 to Brooks et al. These include polyamide, polyester, polysulfone, polycarbonate, and polyamide-imide resin membranes.

Also useful are the microporous sheet materials having one or more distinct strata and made of fibrous material laid down on a substrate from a slurry thereof. Such materials are described in U.S. Pat. No. 3,238,056 dated Mar. 1, 1966 to David B. Pall and Cyril Keedwell; No. 3,246,767 dated Apr. 19, 1966 to David B. Pall and Cyril Keedwell; No. 3,353,682 dated Nov. 21, 1967 to David B. Pall and Cyril Keedwell; and No. 3,573,158 dated Mar. 30, 1971 to David B. Pall and Cyril Keedwell.

The microporous fibrous layer can be self-supporting or supported on the substrate on which the layer is laid down. The layers can be combined in multilayered laminates or composites, of which at least one layer and preferably each layer is microporous, and of a sufficiently small pore size to quantitatively remove bacteria. Such microporous sheet material is characterized by a voids volume in excess of 75%, obtained by selection of the particulate material of which the microporous layer is composed. The particulate material comprises fibrous material in an amount of at least 5% and preferably of at least 15% up to 100% and optionally nonfibrous particulate material in an amount from 0 up to 85%. Details on the formation of these layers will be found in the patents referred to.

Fibrous material is preferred as the particulate material, because of its versatility, greater ease of deposition, and greater strength-imparting properties, and because fibers can be oriented by liquid flow or absence of liquid flow so as to be deposited in a plane approximately parallel to the plane of the layer. A great variety of diameters of fibers are available, thus making it possible to achieve a very large assortment of mixtures of different diameter fibers, for making fibrous material of any porosity, and such fibers can be made of any length, within the stated range, so as to take advantage of the greater cohesiveness of a layer of long fibers, as compared to granular material layers. Typical fibrous materials include glass and quartz, ceramics, asbestos, potassium titanate, colloidal aluminum oxide ("Baymal"), aluminum silicate, silicon carbide whiskers, mineral wool, regenerated cellulose, microcrystalline cellulose, polystyrene, polyvinyl chloride, polyvinylidene chloride, polyacrylonitrile, polyethylene, polypropylene, rubber, polymers of terephthalic acid and ethylene glycol, polyamides, casein fibers, zein fibers, cellulose acetate, viscose rayon, hemp, jute, linen, cotton, silk, wool, mohair, paper, metallic fibers such as iron, copper, aluminum, stainless steel, brass, Monel, silver and titanium, and clays with acicular lath-like or needle-like particles, such as the montmorillonite, sepiolite, palygorskite, and attapulgite clays of this type.

The layers can be advantageously modified by employing a mixture of long and short fibers. The long fibers can be of an average length not less than the average pore size of the foramina of the support or mesh screen, and form the first thin stratum thereon. Thereafter, a substantially uniform intermediate stratum of short fibers can be laid down on the first stratum, and then finally a mixture of clumped and separate long and short fibers as the top stratum. Such a mixture of fibrous material should comprise from about ½ to about 30%, and preferably from about 2 to about 15%, by weight of long fibers having an average length as great as the average pore size of the foramina of the coarse support substrate or mesh screen. The diameter of the long fibers should be less than about 10 times the diameter of the small fibers which comprise the rest of the mixture, and should preferably be less than about three times the diameter of the small fibers. Employment of more than 30% by weight of long fibers in the fibrous material mixture affords no significant advantages, but will only provide a coarser filter medium.

The fibrous material employed in the mixture of various size fibers, if it is too long, or agglomerated, can be broken down into such a length that the desired pore size can be formed. Thus, for example, if the fibers are supplied in bundles which are not readily dispersible in water, the bundles should be broken up by a high shearing action or by grinding, so that the ratio of the length of the fiber to the diameter of the fibers is within the range from about 50:1 to 5000:1, and preferably within the range from about 350:1 to about 1500:1. Such fibers can be broken up with the use of conventional mechanical equipment, such as high speed propellers, grinding equipment, and beaters, such as the Holland and Jordan beaters. Thus, for example, if bundles of asbestos are to be used as fibrous filter material, the bundles can be broken down by the use of Holland or Jordan beaters, or by ball milling in a nonionic detergent-water solution to break down and separate the fibers from one another. Oversized asbestos can be removed from such a mixture by the use of liquid cyclones, such as hydroclones, which collect the desired short fiber material, free of the oversized material. Where asbestos is employed, the use of high speed propellers to generate high shearing action has been found to be inadequate to break up the bundles of fibers. However, where asbestos is used as the long fiber-containing material, grinding or shearing action, such as in a Cowles dissolver, can be employed since a small number of fibers having a diameter to length greater than 5000 can be tolerated.

A mixture of long and short fiber-containing filter material is also employed in the filter material, where special properties are to be imparted to the filter medium, such as, for example, good dirt capacity, good flow-through, and high filtering power, good mechanical strength, and the like.

Nonfibrous particulate materials can be used in admixture with fibrous materials. However, in order to achieve the requisite microporosity and voids volume, it is essential to employ at least five parts by weight of fibrous material for every ninety five parts of nonfibrous materials. When nonfibrous particles are employed, they should have an average diameter not exceeding 25 microns, and preferably not less than one-half the diameter of the fibers.

Those nonfibrous materials containing a fine internal structure or porosity are preferred, for maximum voids volume. Porous diatomaceous earth is particularly useful, inasmuch as each particle acts as a small filter having pores of from 0.1 to 10μ. The collection of dirt in these pores does not result in filter clogging since the fluid can flow around the particles.

Nonporous particulate materials restrict fluid flow and reduce voids volume. However, they are useful if this detriment can be accepted. Adsorbent materials are especially useful. Particles intended to be leached by the fluid, such as pH control compounds and bactericides, increase voids volume concomitantly with lodging of contaminants in the filter pores.

Typical nonfibrous particulate materials are diatomaceous earth, magnesia, silica, talc, silica gel, alumina, quartz, carbon, activated carbon, clays, synthetic resins and cellulose derivatives, such as polyethylene, polyvinyl chloride, polystyrene, polypropylene, ureaformaldehyde, phenol-formaldehyde, polytetrafluoroethylene, polytrifluorochloroethylene, polymers of terephthalic acid and ethylene glycol, polyacrylonitrile, ethyl cellulose, polyamides and cellulose acetate-propionate, and metal particles such as aluminum, silver, platinum, iron, copper, nickel, chromium and titanium and metal alloys of all kinds, such as Monel, brass, stainless steel, bronze, Inconel, cupronickel, Hastelloy, beryllium, and copper.

Figure 6:
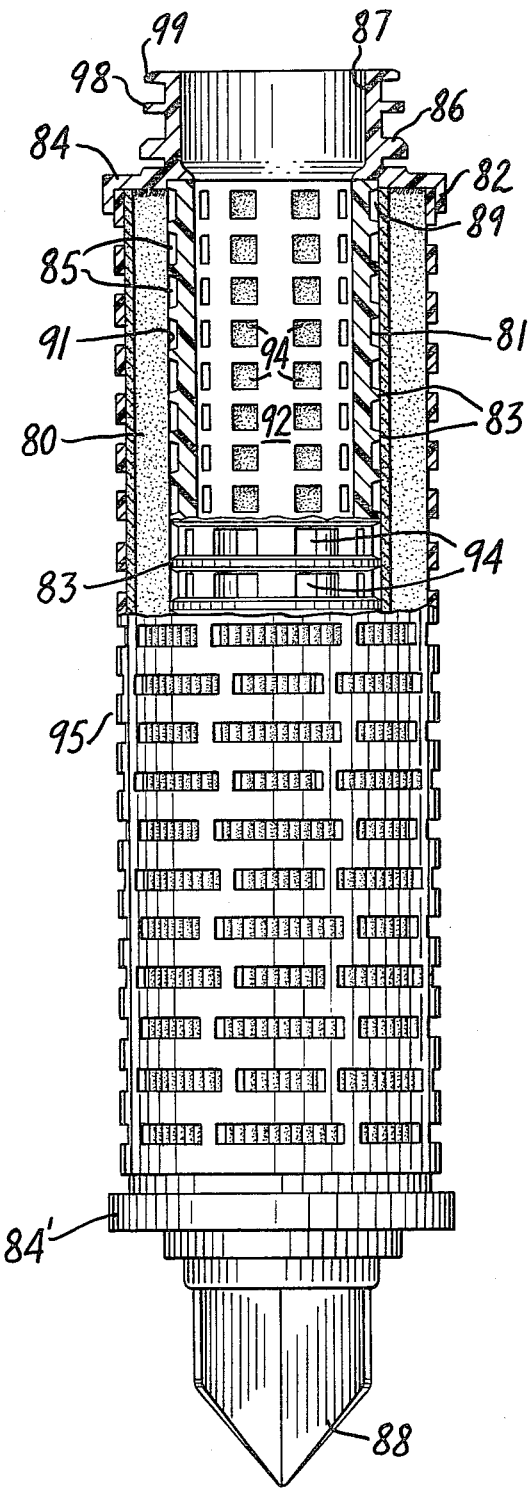

A typical bacterial-retentive filter element of the invention as shown in FIG. 6 comprises a cylindrical core 81 placed in abutting relationship to constitute the internal support core for the corrugated microporous filter element 80, of, for example, nylon membrane having a removal rating a less than 0.3 μm. The element encloses the core 81 tightly in such a manner that inner bases 91 of the corrugations are in contact with the rib tops 83 on the outer surface of the core.

The depressed portions or grooves 85 between the raised portions or ribs 83 of the core 81 serve as channels for the passage of filtrate from the filter 80 to the openings 94 of the core, facilitating passage of fluid from the filter 80 to the central passage 92 for filtrate flow enclosed by the core 81.

The external cage or sheath 95 encloses the filter 80 and retains the corrugations between it and the core 81.

The entire filter element is held together by the end caps 84, 84' each of which is provided with an outer flange 82 retaining the corrugated filter, and a central internally raised portion 86 including in cap 84 of flanged aperture 87 and in cap 84' a spike 88, and abutting the end 89 of the core sections 81 as an internal support therefor. Cap 84 on the raised portion 86 has two externally raised portions 98 and 99 which are adapted to form a tight seal with a gasket in the filter assembly in which the filter element is used. The raised portion 86 holds the core support firmly in position, and in cooperation with the end flanges 89 thereof and the filter 80 and flange 82 prevents both lateral and lengthwise displacement of the core sections 81 and filter 80.

The end caps 84 are held in position by bonding to the filter 80 and core sections 81. The aperture 87 is adapted to fit with existing filtrate flow lines of the filter assembly, or with another filter element, via a sealing gasket (not shown).

In operation, fluid to be filtered passes through the filter element from the outside towards the inside, first entering the filter 80, then flowing along a groove 85 formed by the depressed portion of the core sections 81, to and through the opening 94 and into the central passage 92 enclosed by the core sections, whence it can be drawn off through the central opening 87 in the end cap 84.

While the invention has been described with principal emphasis on an air purification system and a process for purifying air, it will be apparent to those skilled in the art that this apparatus with a suitable choice of sorbent can be used for the separation of one or more gaseous components from a gaseous mixture and obtaining a quite pure gaseous effluent. In such a case, the adsorbed component can also be removed from the sorbent by application of heat, and optionally, in addition, a reduction in pressure, during regeneration. Thus, the process can be used for the separation of hydrogen from petroleum hydrocarbon streams and other gas mixtures containing the same, for the separation of oxygen from nitrogen, for the separation of olefins from saturated hydrocarbons, and the like. Those skilled in the art are aware of sorbents which can be used for this purpose.

In most cases, sorbents useful for the removal of moisture from air can also be used, preferentially to adsorb one or more gas components from a mixture thereof, such as activated carbon, glass wool, adsorbent cotton, metal oxides and clays such as attapulgite and bentonite, fuller's earth, bone char and natural and synthetic zeolites. The zeolites are particularly effective for the removal of nitrogen, hydrogen and olefins, such as ethylene or propylene, from a mixture with propane and higher paraffin hydrocarbons, or butene or higher olefins. The selectivity of a zeolite is dependent upon the pore size of the material. The available literature shows the selective adsorptivity of the available zeolites, so that the selection of a material for a particular purpose is rather simple and forms no part of the instant invention.

In some cases, the sorbent can be used to separate a plurality of materials in a single pass. Activated alumina, for example, will adsorb both moisture vapor and carbon dioxide, in contrast to Mobilbeads which will adsorb only water vapor in such a mixture.

The apparatus employed for this purpose will be the same as that described and shown in FIGS. 1 to 6 inclusive, and the process is also as described, suitably modified according to the proportions of the components to be separated, the operating pressure and temperature and the volume of available sorbent.

It will, however, be understood that the process is of particular application in the purification of air for pharmaceutical uses, and that this is the preferred embodiment of the invention.

The following Example illustrates application of the apparatus of FIG. 1 to the purification of compressed air. In the Example, liquid hydrocarbons (oil) content of the air at various stages of the flow sequence were measured by two methods.

1. Johnson Service A-4001 Oil Indicator

This device correlates the rate of color change in a packed column with oil concentration. Oil is stopped by the dense packing and is colored by a red oil-soluble dye. The tubes pass two cubic inches of air per minute per PSI system pressure. A rate of travel versus system pressure for constant lines of oil concentration chart is provided by the manufacturer, Johnson Service Corporation, Milwaukee, Wis.

2. A gravimetric sampler using a 35 mm disc of Hollingsworth and Vose H-93 (HEPA, glass medium) is run in parallel with the Johnson Service Indicator. Filter discs are washed in filtered Freon TF and desiccated to a constant weight prior to installation. Differential pressure is monitored across the disc during sampling (sample flow rate of 0.5 SCFM at 80 PSIG established by sampler critical orifice) to preclude liquid saturation and by-pass. This allows an optimum sample size in order to maximize accuracy.

Discs are desiccated to a constant weight on removal and liquid hydrocarbon concentration calculated:

$$\text{Concentration (ppm wt.)} = \frac{\text{Wt. gain (grams)}}{\text{time (hrs)}} \times 980$$

Hydrocarbon vapors were analyzed by two methods:

1. Total Hydrocarbons, reported as ppmC (vol.) are measured from the compressor inlet to the purification system effluent using a Beckman Model 400 Hydrocarbon Analyzer. A 40% hydrogen/60% nitrogen fuel mixture is used. A 0.2 μm absolute 47 mm membrane disc is incorporated at sample input to prevent liquid fouling readings as assurance that the disc would not alter the results. Sample gases of 6.8 ppm methane and 5.0 ppm methane/4.0 ppm ethane in air are used for calibration.

2. Gas chromatography (direct sampling) is employed to qualify and quantify air samples. An F & M Model 609 Flame Ionization Gas Chromatograph with hydrogen flame ionization detector is used for constant temperature and time/temperature programmed sampling. The column is an Applied Science Labs 80–100 mesh Poropak Q 8 ft.×⅛ in. O.D. stainless steel with stationary phase.

Carrier gas is hydrocarbon-free air (Linde); combustion gases are hydrocarbon-free air (Linde) and ultra high purity hydrogen (Matheson); and a custom mixture of 5.0 ppm methane/4.0 ppm ethane/balance zero air (Linde) is the calibration gas. A two-position sampling valve is used to inject a fixed volume loop of sample (normally flowing through loop to vent) with the carrier gas.

Moisture (reported as dewpoint °F at system pressure) is monitored with an Alnor Type 7000 dewpointer. This device relates the pressure required to produce a visible "fog" from a sample rapidly expanded (temperature drop associated with adiabatic expansion).

The limit of useful component life, specifically disposable filter cartridge and adsorbent life, is determined as an unacceptably high pressure drop across the filter a rated flow, significant reduction in contaminant removal capability, or both.

The following data show contamination levels at sample points throughout the apparatus of FIG. 1 after 10,500 hours of continuous operation:

1. Hydrocarbon aerosols:

Table I presents typical data over the duration of the test:

TABLE I

| Sample Point | Aerosol Initial | Concentration (ppm wt/wt) After 10,500 hours |
|---|---|---|
| A Inlet | 5.96 | 3.36 |
| D After Prefilter | 0.27 | 0.25 |
| H After Oil Vapor Adsorber | 0.127 | 0.047 |
| J After Filter | — | 0.006 |
| M After-Outlet | — | 0* |

*No change in Johnson Service Indicator in 10,500 hours and zero weight gain of gravimetric disc in 5000 hours.

Gravimetric sampling is performed coincidentally with Johnson Service sampling. As the gravimetric method requires a larger sample and the influent as well as intermediate liquid hydrocarbon concentrations varied with time, direct comparison is not possible. Typical readings are given in Table II:

TABLE II

| Location | Johnson Service A4001 | Gravimetric |
|---|---|---|
| A Influent | 4.0,5.0 | 5.0,5.1,7.0 |
| J After-Prefilter | 0.36,0.48,0.32,0.36 | 0.61 |

2. Hydrocarbon Vapors:

Typical total hydrocarbons (using the Beckman Model 400 Analyzer) are presented in Table III:

TABLE III

| Total Hydrocarbons ppmC (Vol) | | | |
|---|---|---|---|
| After Prefilter D | After Dryer G | After Oil Vapor Adsorber H | At Outlet M |
| *2.6 | 1.90 | 1.90 | 1.60 |
| **15.25 | 1.90 | | 1.50 |
| **24.55 | 2.05 | | 1.69 |
| **15.80 | 2.00 | | 1.65 |
| **95.100 | 1.90 | 1.85 | 1.60 |
| **45.55 | 2.00 | 1.80 | 1.55 |

*Ambient air. Concentration at compressor intake at time of this sample was 3.6 ppmC. Range of intake total hydrocarbons was 3.20 ppC.
**Ethanol injection at purification system inlet to synthesize worst case field conditions.

Gas chromatographic analysis was carried out under the following conditions:
Column: 8 ft×⅛ in O.D. stainless with 80–100 mesh Porapak Q Phase
Column Temperature: Isothermal 50° C.–150° C.
Detector Block: 100° C.
Range: 1
Attenuations: 16-2
Flow Rates: Carrier—107 scc/min
Combustion—$H_2$ 576 scc/min Air 2.1 SLPM
Sample—Constant pressure and flow for all trials The gas chromatographic analysis indicated only methane present downstream of the desiccant dryer and are given in Table IV. To eliminate the possible interference of small quantities of hydrocarbon aerosols in these experiments, a 47 mm 0.2 μm absolute filter disc was employed at all sample points.

TABLE IV

| | Total Hydrocarbons ppmC (Vol) | |
|---|---|---|
| Sample Point | Without Filter | With Filter |
| After Dryer G | 2.30 | 2.10 |
| After Oil Vapor Adsorber H | 2.10 | 1.90 |
| At Outlet M | 1.95 | 1.90 |

3. Water Vapor
Typical dewpoints are given in Table V:

TABLE V

| | Dewpoint (°F.) at 80 PSIG | |
|---|---|---|
| Sample Point | Initial | After 10,500 hours |
| After Prefilter D | +53 | +56 |
| After Dryer G | −53 | −41 |
| At Outlet M | −53 | −40 |

4. Component Life
Component pressure drop versus time is shown in Table VI, with component replacements noted:

TABLE VI

| | Pressure Drop (PSI) | |
|---|---|---|
| Component | Initial | After 10,500 hours |
| *Prefilter D | 0.30 | 2.45 |
| Dryer G | —*** | 8.85 |
| Carbon Adsorber H | 0.16 | 0.13 |
| Afterfilter J | 0.20 | 0.21 |
| **Final Filter K | 0.85 | 1.15 |
| Total | 9.6 | 12.2 |

*Prefilter cartridge replaced after 1710 hours and 7380 hours.
**Final filter cartridge replaced after 8369 hours.
***Initial Dryer pressure drop not recorded.

It is apparent from the above data that the test system, operating off an oil-lubricated compressor, continuously provided compressed air of a quality consistent with the proposed Current Good Manufacturing Practices for Large Volume Parenterals:

1. Elimination of particulates by prefiltration and absolute final filtration
2. Control of moisture to a −40° F. or lower dewpoint at pressure
3. Continuous removal of hydrocarbon vapors (exclusive of methane and ethane)
4. Reduction of hydrocarbon (oil) aerosols to below detectible levels The purification system components are interdependent and the elimination of any component may affect overall performance. Additional components may be desirable for particular applications (two series prefilters may be used to protect dryer desiccant for a system with high liquid oil or water levels), but no benefits from removal of the test system's components are apparent. Protected by the dryer, the oil vapor adsorber can act as a back-up bed to remove hydrocarbons not eliminated at the dryer, remove hydrocarbons generated between the dryer and adsorber (ex.: original piping fed by an oil-lubricated compressor), and short-term water and hydrocarbon vapor removal in the event of interrupted dryer operation.

Substantial quantities of hydrocarbons in both vapor and liquid states may exist at the compressor intake. Oil-free compressors will not remove ambient hydrocarbons. As all components of the purification system would be required for either oil-lubricated or oil-free compressors to produce the test system effluent levels, oil-lubricated compressors should be selected in view of their low initial and operating costs.

Oil-free compressors should be used in applications unsuited to oil-lubricated types such as for compression of oxygen (safety), where no suitable lubricants are available (such as for very low temperatures), and where the gas attacks the lubricant (chlorine and borontrifluoride).

Correlation between the total hydrocarbon analyzer and gas chromatograph was good. The results of sampling total hydrocarbons with and without in-line absolute filtration indicates that the activated carbon adsorber is removing trace (0.2 ppmC) hydrocarbons which are not evident on the gas chromatograph curves. Gravimetric evaluation of hydrocarbon aerosols indicates that the easier-to-implement Johnson Service A-4001 Oil Indicator is a satisfactory means of liquid oil quantification.

Having regard to the foregoing disclosure, the following is regarded as inventive and patentable embodiments thereof:

1. An air purification system capable of removing substantially quantitatively commonly occurring gaseous liquid and solid contaminants, including water and hydrocarbons, from compressed air, thereby ensuring hydrocarbon-free moisture-free and particulate-and microbial-solid-contaminant-free compressed air, ready for application in pharmaceutical uses, comprising, in combination, and in the sequence indicated: p1 (1) a coalescer filter separating and removing hydrocarbon droplets and water droplets;

(2) an adsorbent dryer sorbing water vapor and hydrocarbon aerosols at least in part on particulate desiccant;

(3) an oil vapor adsorber sorbing hydrocarbon vapor and hydrocarbon aerosols at least in part on particulate activated sorbent;

(4) an after-filter separating and removing particulate solids larger than bacterial dimensions; and (5) a bacterial-retentive final filter separating and removing particulate solids of bacterial dimensions and any remaining hydrocarbon aerosols.

2. An air purification system according to claim 1 in which the coalescer filter comprises a first stage coalescer in which entrained liquid droplets are coalesced into droplets sufficiently large to be affected by gravity, a second stage coalescer in which the remaining portions of partially condensed droplets are further coalesced, and means for collecting and draining off liquid from the coalescer filter.

3. An air purification system according to claim 2 in which the first stage coalescer is a nonwoven fibrous mat.

4. An air purification system according to claim 3 in which the fibrous mat is of glass fibers.

5. An air purification system according to claim 2 in which the second stage coalescer is a polyurethane foam sheet.

6. An air purification system according to claim 2 in which the second stage coalescer is a porous fibrous mat.

7. An air purification system according to claim 6 in which the fibrous mat is of glass fibers.

8. An air purification system according to claim 6 in which the fibrous mat is of polypropylene fibers.

9. An air purification system according to claim 2 in which the first and second stage coalescers are each tubular and concentric with the first stage coalescer internal and the second stage coalescer external.

10. An air purification system according to claim 9 in which the first stage coalescer comprises at least one layer of epoxy-impregnated cellulose paper and at least one layer of epoxy-bonded fibrous mat of glass fibers, and the second stage coalescer comprises a foamed polyurethane sheet.

11. An air purification system according to claim 9 in which the first stage coalescer comprises at least one layer of epoxy-impregnated cellulose paper and at least one layer of epoxy-bonded fibrous mat of glass fibers, and the second stage coalescer comprises a polypropylene fibrous mat.

12. An air purification system according to claim 1 in which the adsorbent dryer is heaterless.

13. An air purification system according to claim 12 in which the dryer comprises two beds, one of which is on-stream for adsorption while the other is off-stream for regeneration.

14. An air purification system according to claim 12 in which the desiccant is activated alumina.

15. An air purification system according to claim 12 in which the desiccant is activated silica gel.

16. An air purification system according to claim 12 in which the desiccant is activated molecular sieve.

17. An air purification system according to claim 1 in which the oil vapor adsorber comprises a vessel with a chamber therein comprising a bed of particulate activated sorbent.

18. An air purification system according to claim 17 in which the activated sorbent is activated carbon.

19. An air purification system according to claim 17 in which the activated sorbent is activated alumina.

20. An air purification system according to claim 1 in which the after-filter comprises a plurality of fibrous filter sheets of differing pore size, arranged in sequence of fluid flow therethrough according to decreasing pore size.

21. An air purification system according to claim 20 in which the fibrous filter sheets are free from synthetic resin and binders.

22. An air purification system according to claim 20 in which the fibrous filter sheets comprise cellulose fibers.

23. An air purification system according to claim 20 in which the fibrous filter sheets comprise polypropylene fibers.

24. An air purification system according to claim 1 in which the bacterial-retentive final filter comprises a microporous filter sheet having a pore size of less than 3 microns, small enough to quantitatively remove bacteria, fungi and microorganisms.

25. An air purification system according to claim 24 in which the microporous filter sheet comprises a synthetic resin filter membrane.

26. An air purification system according to claim 25 in which the synthetic resin filter membrane is a polyamide membrane.

27. An air purification system according to claim 24 in which the microporous sheet material comprises at least one stratum of fibrous material laid down on a substrate from a slurry thereof.

28. An air purification system according to claim 1 in which the coalescer filter comprises a first stage coalescer in which entrained liquid droplets are coalesced into droplets sufficiently large to be affected by gravity, a second stage coalescer in which the remaining portions of partially condensed droplets are further coalesced, and means for collecting and draining off liquid from the coalescer filter; the adsorbent dryer is heaterless; the oil vapor adsorber comprises a vessel with a chamber therein comprising a bed of particulate activated sorbent; the after-filter comprises a plurality of fibrous filter sheets of differing pore size, arranged in sequence of fluid flow therethrough according to decreasing pore size; and the bacterial-retentive final filter comprises a microporous filter sheet having a pore size of less than 3 microns, small enough to quantitatively remove bacteria, fungi and microorganisms.

29. An air purification system according to claim 28 in which the first and second stage coalescers are each tubular and concentric, with the first stage coalescer internal and the second stage coalescer external.

30. An air purification system according to claim 28 in which the dryer comprises two beds, one of which is on-stream for adsorption while the other is off-stream for regeneration.

31. An air purification system according to claim 30 in which the desiccant is activated alumina.

32. An air purification system according to claim 30 in which the desiccant is activated silica gel.

33. An air purification system according to claim 30 in which the desiccant is activated molecular sieve.

34. An air purification system according to claim 28 in which the activated sorbent is activated carbon.

35. An air purification system according to claim 28 in which the activated sorbent is activated alumina.

36. An air purification system according to claim 28 in which the microporous filter sheet comprises a synthetic resin filter membrane.

37. An air purification system according to claim 36 in which the synthetic resin filter membrane is a polyamide membrane.

38. A air compressor and purification system capable of delivering hydrocarbon-free moisture-free and particulate- and microbial-solid-contaminant-free compressed air, ready for application in pharmaceutical uses, comprising, in combination, and in the sequence indicated:
  (1) an air compressor;
  (2) an after-cooler;
  (3) a compressed air receiver;
  (4) a coalescer filter separating and removing hydrocarbon droplets and water droplets;
  (5) an adsorbent dryer sorbing water vapor and hydrocarbon aerosols at least in part on particulate desiccant;
  (6) an oil vapor adsorber sorbing hydrocarbon vapor and hydrocarbon aerosols at least in part on particulate activated sorbent;
  (7) an after-filter separating and removing particulate solids larger than bacterial dimensions; and
  (8) a bacterial-retentive final filter separating and removing particulate solids of bacterial dimensions and any remaining hydrocarbon aerosols.

* * * * *

UNITED STATES PATENT AND TRADEMARK OFFICE
CERTIFICATE OF CORRECTION

PATENT NO. : 4,231,768
DATED : November 4, 1980
INVENTOR(S) : Chesterfield F. Seibert et al It is certified that error appears in the above—identified patent and that said Letters Patent is hereby corrected as shown below:

Column 2, line 24 :
Under Hydrocarbon:    "Ethane" should be --Ethene--.
Column 3, line 56 :   "mose" should be --most--.
Column 6, line 18 :   "if" should be --it--.
Column 8, line 48 :   "terepthalic" should be --terephthalic--
Column 12, line 5 :   "progressivly" should be --progressively--.
Column 21, line 33 :  "of" should be --a--.
Column 25, line 60:   after "indicated:", please delete --p1--.

Signed and Sealed this

Twenty-ninth Day of September 1981

[SEAL]

Attest:

GERALD J. MOSSINGHOFF

Attesting Officer      Commissioner of Patents and Trademarks